United States Patent [19]

Fredzell

[11] 4,433,430
[45] Feb. 21, 1984

[54] APPARATUS FOR THE AREAL RECORDING OF X-RAY IMAGES

[75] Inventor: Georg Fredzell, Stockholm, Sweden

[73] Assignee: Siemens Aktiengesellschaft, Berlin & Munich, Fed. Rep. of Germany

[21] Appl. No.: 375,004

[22] Filed: May 5, 1982

[30] Foreign Application Priority Data

May 27, 1981 [DE] Fed. Rep. of Germany ....... 3121176

[51] Int. Cl.$^3$ ............................................. G03B 41/16
[52] U.S. Cl. ..................................... 378/108; 378/146
[58] Field of Search ................................ 378/108, 146

[56] References Cited

U.S. PATENT DOCUMENTS

| | | | |
|---|---|---|---|
| 4,051,377 | 9/1977 | Kemner | 378/108 |
| 4,097,748 | 6/1978 | Monvoisen | 378/146 |
| 4,333,012 | 6/1982 | Furuichi | 378/108 |

OTHER PUBLICATIONS

Erich Krestel, *Imaging Systems for Medical Diagnostics*, Siemens AG Publishing House, Berlin & Munich, 1980, pp. 190-201.

Primary Examiner—Craig E. Church
Attorney, Agent, or Firm—Hill, Van Santen, Steadman & Simpson

[57] ABSTRACT

In order to prevent the stray radiation produced in a subject from reaching the image recording carrier a slit diaphragm mechanism is already known in which the employed diaphragms are moved during the radiographic recording relatively to the subject and image recording carrier. In order to attain, in addition to the extensive secondary ray blanking-out within a single radiographic recording, an optimum exposure for subject parts of strongly varying density in a simple and reliable fashion, it is proposed in accordance with the disclosure that the diaphragm exhibit an additional aperture, whereby the radiation beam passing through this additional aperture irradiates a subject region to be imaged chronologically later and impinges on a detector, whose signal is supplied to a device for the control of the exposure. Through the device the high voltage of the x-ray source can be particularly advantageously controlled.

8 Claims, 4 Drawing Figures

APPARATUS FOR THE AREAL RECORDING OF X-RAY IMAGES

BACKGROUND OF THE INVENTION

The invention relates to an apparatus for the recording of x-ray images, comprising an x-ray source, an image recording carrier, as well as at least one diaphragm, arranged between the x-ray source and a subject to be examined and exhibiting at least one aperture, for the purpose of generating a first radiation beam, in which the diaphragm is moved relative to the subject and the image recording carrier in such a fashion that the subject is areally irradiated and imaged.

The information content in an x-ray image today is primarily restricted by the secondary radiation which is superimposed on the desired information. For certain subjects this stray radiation can amount to up to 70%. In order to reduce this contrast-reducing effect of stray radiation, already various stray radiation screens (Erich Krestel, *Imaging Systems for Medical Diagnostics*, Siemens AG Publisher, Berlin and Munich, 1980, pp 190 to 201) are known. In particular, a slit diaphragm mechanism is also known therefrom in which, through a first slit diaphragm between the x-ray source and the subject, and selectively an additional slit diaphragm between the subject and the image recording carrier, delineate from a greater radiation field a narrow strip radiation beam cross section in which the stray radiation is low. In order to image the entire subject the slit diaphragms must be moved over the image field during radiographic recording.

A further contrast-reducing, and hence information-limiting, factor results from the difficulty of adapting the exposure to various parts of the subject if the latter exhibit great variations in density and hence in x-ray absorption.

Too soft x-radiation is entirely absorbed in the denser subject regions, so that the latter can virtually not be imaged. If one selects so hard an x-radiation that all subject regions are imaged, this impairs the contrast, specifically in the regions of lower density. A certain remedy is here provided by additional absorption layers, so-called Dogers, which are arranged over the subject regions of low density. However, through these "Dogers", also the danger of an image falsification exists, since they are jointly imaged, as a consequence of which an additional image is superimposed on the actual subject image. Moreover, they cause stray radiation.

The most reliable way for high-contrast imaging of variously dense subject parts previously consisted in making several radiographs with varying exposure in which respectively only partial regions were optimally exposed and hence imaged in high-contrast fashion. The varying exposure was adjusted through alteration of the exposure time.

SUMMARY OF THE INVENTION

An important object underlying the present invention, in the case of an apparatus of the type initially cited, consists, within a single radiographic recording, in addition to an extensive secondary radiation blanking-out, in obtaining, in a simple and reliable fashion, an optimum exposure for subject parts of varying density.

In accordance with the invention, this object is achieved in that the diaphragm exhibits at least one additional aperture arranged in such a fashion that the additional radiation beam passing through this aperture irradiates a subject region to be imaged later chronologically, and that, between the subject and the image recording carrier in the region of the additional radiation beam, at least one detector for the direct sensing of the x-radiation penetrating the subject is provided, whose signal is supplied to a device which, in dependence thereupon, controls the radiation dose reaching the image recording carrier for the region to be imaged later. The detector thus exactly detects respectively the x-radiation penetrating the subject for the next-following, or possibly also a still later, image region.

As long as the sensed radiation dose lies within the contrast range of the image recording carrier the exposure at the time at which the subject region detected by the detector comes to imaging is not altered. Only when the sensed radiation dose comes to lie outside the contrast range, i.e., when a large density difference is present in the subject regions, does the device alter the exposure in such a fashion that it again imparts a signal within the contrast range. The exposure alteration proceeds with a time delay which corresponds to the chronological interval of the subject region detected by the detector from the subject region to be imaged.

With the aid of this apparatus it is therefore possible to image subjects with strongly varying density in a single image in all subject parts, with high contrast.

In a further development of the invention it is provided that, between the subject and the image recording carrier, an additional diaphragm with at least one aperture in the region of the first radiation beam is arranged. By means of this additional diaphragm, a great portion of the stray radiation produced in the subject is intercepted, so that the result is an additional improvement in image quality. A simplification of the control of the relative movement between the diphragms, on the one hand, and the subject and image recording carrier, on the other hand, results if slit diaphragms are provided as diaphragms. With a one-time traversing of the image field the entire radiographic recording can thereby be made.

In order to also be able to detect density fluctuations of the subject perpendicular to the movement direction, in an advantageous further development of the inventive apparatus with slit diaphragms, it is provided that a detector row is disposed in the region of the additional radiation beam, whose individual detectors, in a preselectable interconnection, deliver the signal for the device for the control of the radiation dose. The signals of the individual detectors can then, equally or differently weighted, be supplied to the device for the determination of the correct exposure. If, for example, one knows prior to a radiographic recording that there will be greater density fluctuations only in a specific strip of the entire image field, then one can employ only the detectors covering this strip for the exposure measurement, and hence increase the quality of this measurement.

The detector(s) can be arranged with respect to the ray direction before the additional diaphragm or also behind such diaphragm. In the latter instance, the diaphragm must exhibit an additional aperture in the region of the detector or of the detectors. A simple and mechanically stable embodiment provides that the detector, or detectors, respectively, is, or are, respectively, fixedly connected with the additional diaphragm.

The device can alter the exposure time by controlling the speed of the relative movement. Through the development of new types of x-ray sources it is also possible, particularly advantageously, for the device to control the high voltage of the x-ray source. This high voltage is an even better parameter for an automatic exposure control than the exposure time.

Altogether there thus results an apparatus for the recording of x-ray images which unites in itself a combination of effective secondary ray blanking out, optimum image quality in all regions, and high voltage-dependent automatic exposure control.

In the following exemplary embodiments of the invention shall be described and explained on the basis of four Figures on the accompanying drawing sheet; and other objects, features and advantages will be apparent from this detailed disclosure and from the appended claims.

DETAILED DESCRIPTION

Figure 1:
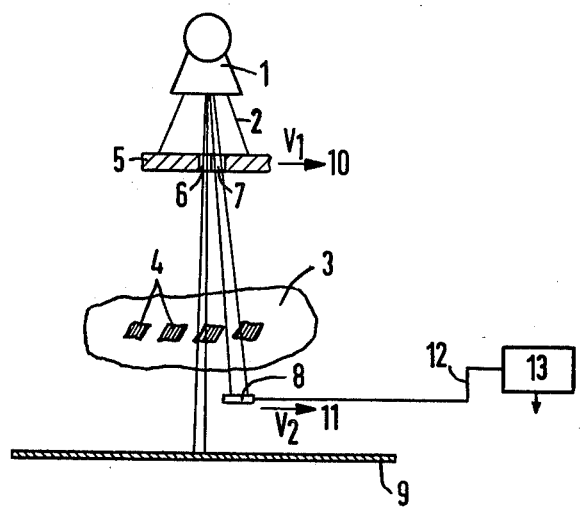
FIG. 1 shows a schematic illustration of apparatus according to the invention for the recording of x-ray images.

The same parts are provided in all Figures with the same reference characters.

In FIG. 1, 1 designates an x-ray source which, for example, illuminates the entire subject field. In the cone of rays 2 of this x-ray source 1 there is disposed as subject the portion of a body 3 with a spinal column 4. Between the x-ray source 1 and the subject there is disposed a diaphragm 5 with a first aperture 6 and a second aperture 7, and with a length at least twice the span of the x-ray beam impinging thereon, and with a width to block the x-ray beam except at apertures 6 and 7. Viewed in the ray direction, behind the subject 3 there is disposed, as image recording carrier, a film plate 9. The radiation beam passing through the first aperture 6 of the diaphragm 5 irradiates the body 3 and subsequently reaches the film plate 9. The radiation beam diaphragmed out by means of the additional aperture 7 of the diaphragm 5 likewise irradiates the body 3 and subsequently reaches a detector 8 which is arranged between the subject and the image recording carrier. In this exemplary embodiment, the diaphragm 5 is moved in the direction of the arrow 10 with a velocity $v_1$. In synchronism therewith the detector 8 is displaced in direction of the arrow 11 with a velocity $v_2$. The ratio of the velocities $v_1$ and $v_2$ is so selected that the radiation beam passing through the aperture 7 of the diaphragm 5 always impinges on the detector 8.

The detector output signal is transmitted via a line 12 to a device 13 which serves as exposure meter and as a control device for controlling the velocities of the diaphragm 5 and of the detector 8.

Figure 3:
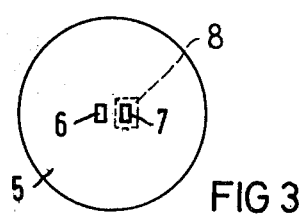
FIGS. 3 and 4 show respective different diaphragm configurations.

The function of this apparatus is the following:

The x-rays penetrate the subject 3 more or less, depending upon the density and the absorption properties of the individual subject parts. Via the detector 8 and the device 13 the correct exposure for each individual subject region is determined. When subsequently the diaphragm 5 is displaced to such an extent that the aperture 6 reaches the location in the cone of rays at which previously the aperture 7 was disposed, then, in this exemplary embodiment, with unaltered high voltage of the x-ray source, and hence constant primary radiation, the exposure is adapted to the subject region through alteration of the exposure time, i.e., through variation of the diaphragm velocity. The aperture 6 in the diaphragm 5 can exhibit a square cross section of small dimension, so that the entire image field must be recorded in a line-by-line scanning pattern. A diaphragm 5 of this type with aperture 6 and an additional aperture 7 for the radiation beam reaching the detector 8 is illustrated in plan view in FIG. 3.

Figure 4:
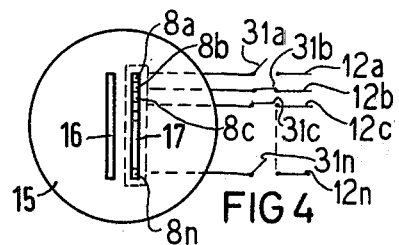

However, a diaphragm 15 with a slit-shaped aperture 16 and an additional slit 17 is also possible, such as is illustrated in plan view in FIG. 4. If, in the case of this arrangement, instead of an individual detector, an entire detector row is employed, then, for example, via the signals of the individual detectors of this detector row, it is possible to average in a linear or also in a weighted fashion. Moreover, it is also possible to employ only individual ones of these detectors selectively for signal generation.

Figure 2:
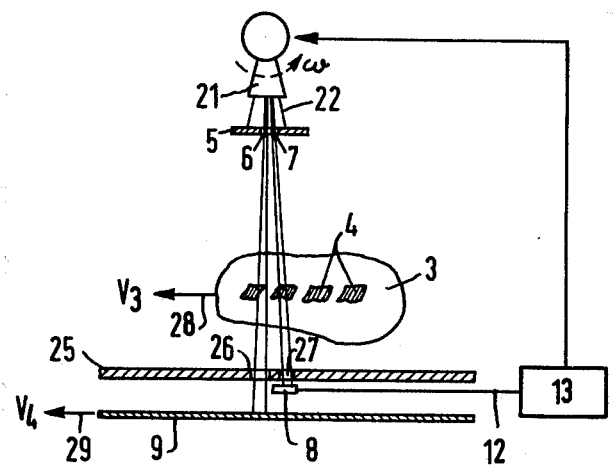
FIG. 2 illustrates a corresponding apparatus with an additional diaphragm.

In FIG. 2, a somewhat modified exemplary embodiment is illustrated. The x-ray source 21 has a smaller angular aperture (or aperture angle) than the source 1 consequently now only illuminates a portion of the subject field. The load for the tube is thereby considerably reduced. In addition to the first diaphragm 5, in this exemplary embodiment, an additional diaphragm 25 is provided which likewise exhibits two apertures 26 and 27, respectively. Through the additional diaphragm 25 the stray radiation issuing from the subject 3 is at least partially suppressed, as a consequence of which the image quality is further increased. In this exemplary embodiment the subject, i.e., the body 3, is moved in the direction of the arrow 28 with a velocity $v_3$, and the film plate 9 is moved in the direction of the arrow 29 with a velocity $v_4$. Likewise, also the two diaphragms 5 and 25 can be moved in the opposite direction synchronously with velocities which correspond to their respective distance from the x-ray source. Moreover, where the diaphragms 5 and 25 are moved, the x-ray source 21 would have to be rotated with a velocity omega in order that the entire subject field is successively irradiated.

In constrast to the exemplary embodiment according to FIG. 1, here through the device 13, the high voltage of the x-ray tube 21 is controlled in order to control the exposure. For this purpose, a special x-ray tube is necessary in which this change is very rapidly possible.

As illustrated in the examples according to the FIGS. 1 and 2, a spinal column 4 is to be imaged as the subject. The latter consists, as is known, of vertebrae and intervertebral disks. The apertures in the diaphragms move along the spinal column in its longitudinal direction. The detector range is disposed spatially and chronologically shortly before the image region to be recorded. As soon as the substantially higher x-ray dose rate, which is allowed to pass through an intervertebral disk, impinges on the detector, the device 13 effects, chronologically delayed, a reduction of the exposure, either through a shorter exposure time, i.e., the relative velocity between subject and diaphragm is increased, or through a lower voltage of the x-ray source.

It will be apparent that many modifications and variations may be made without departing from the scope of the teachings and concepts of the present invention.

Supplementary Discussion

For the sake of diagrammatic illustration, FIG. 4 shows a row of n detectors 8a, 8b, 8c, ..., 8n, disposed in the path of the additional radiation beam transmitted by slit 17. By way of example, FIG. 4 illustrates a case where a preselectable interconnection of the detectors is controlled by respective associated switches 31a, 31b, 31c, ..., 31n. Thus, where a strip region to be scanned by detectors 8b, 8c is to have a relatively great density variation, only switches 31b and 31c are closed. In this case radiation exposure control 13 is provided with reference input values corresponding to the signals from detectors 8b and 8c which would correspond to the contrast range limits of the film plate 9. As long as the radiation dose sensed by detectors 8b and 8c lies within the contrast range of the film plate 9, a constant speed of movement of the beams over the patient region 3 with constant x-ray anode voltage is maintained. If, however, the radiation dose sensed by detectors 8b and 8c comes to lie outside the contrast range of film plate 9, e.g. the dose rate is too high as represented by a summation of the signals from detectors 8b and 8c exceeding an upper dose rate limit reference value, then a control action is initiated by the control 13 after a time delay which would be a function of the separation of slits 16 and 17 and the velocity of the diaphragm plate 15. For example the anode voltage could be reduced by a predetermined amount previously found suitable for the expected density changes along the path of detectors 8b, 8c. Similarly when the output of detectors 8b, 8c fell below a selected lower contrast range limit value previously found suitable for the expected density changes and for film plate 19, the anode voltage could be increased for example by the same predetermined amount. The suitable reference levels for a given film plate 9 and a given number of detectors can be determined by experiment using materials providing the expected maximum and minimum densities to be encountered during the scanning of a given body region. The spacing of slits 16 and 17 and the velocity of movement of diaphragm plate 15 relative to the patient 3 and film plate 9 may be selected to accomodate any necessary time lag in the operation of the x-ray high voltage generator (which may be considered as included within control component 3) to provide a desired increment or decrement in anode voltage. The desired operation of a high voltage generator as here described can readily be implemented by one of ordinary skill in the art.

I claim as my invention:

1. Apparatus for the recording of x-ray images, comprising an x-ray source, an image recording carrier, as well as at least one diaphragm, arranged between the x-ray source and a subject to be examined and exhibiting at least one aperture, for the purpose of producing a first radiation beam, in which the diaphragm is moved relatively to the subject and image recording carrier in such a fashion that the subject is irradiated and imaged in an area fashion, characterized in that the diaphragm (5) exhibits at least one additional aperture (7) arranged in such a fashion that the additional radiation beam passing through said additional aperture (7), irradiates a subject region to be imaged chronologically later, and that, between the subject (3) and the image recording carrier (9) in the region of the additional radiation beam, detector means (8) for the direct sensing of the x-radiation penetrating the subject (3) is provided, and radiation exposure control means (13) coupled with the detector means, which in dependence on the output signal from the detector means, controls the radiation dose, reaching the image recording carrier (9), for the region to be imaged later.

2. Apparatus according to claim 1, characterized in that, between the subject (3) and the image recording carrier (9), an additional diaphragm (25) with at least one aperture (26) is arranged in the region of the first radiation beam.

3. Apparatus according to claim 1, characterized in that the diaphragm (5) is a slit diaphragm.

4. Apparatus according to claim 1, characterized in that said detector means comprises a row of detectors disposed in the path of the additional radiation beam, the individual detectors of said row having a preselectable interconnection for supplying the output signal to said radiation exposure control means.

5. Apparatus according to claim 2, characterized in that the detector means (8) is arranged with respect to the ray direction before the additional diaphragm (25).

6. Apparatus according to claim 2, characterized in that the detector means (8) is arranged with respect to the ray direction behind the additional diaphragm (25) and that the diaphragm (25) exhibits an additional aperture (27) in alignment with said detector means (8).

7. Apparatus according to claim 1, characterized in that the radiation exposure control means (13) controls the velocity of the relative movement.

8. Apparatus according to claim 1, characterized in that the radiation exposure control means (13) controls the high voltage of the x-ray source (21).

* * * * *